US007527480B2

(12) United States Patent
Scurati

(10) Patent No.: US 7,527,480 B2
(45) Date of Patent: May 5, 2009

(54) MICROPUMP FOR INTEGRATED DEVICE FOR BIOLOGICAL ANALYSES

(75) Inventor: Mario Scurati, Milan (IT)

(73) Assignee: STMicroelectronics S.r.l., Agrate Brianza (IT)

( * ) Notice: Subject to any disclaimer, the term of this patent is extended or adjusted under 35 U.S.C. 154(b) by 707 days.

(21) Appl. No.: 10/663,239

(22) Filed: Sep. 16, 2003

(65) Prior Publication Data

US 2004/0141856 A1 Jul. 22, 2004

(30) Foreign Application Priority Data

Sep. 17, 2002 (IT) .......................... TO2002A0809

(51) Int. Cl.
*F04F 3/00* (2006.01)
*C12M 1/34* (2006.01)
*B01L 3/02* (2006.01)

(52) U.S. Cl. ...................... 417/148; 422/68.1; 422/100; 435/6; 435/287.6

(58) Field of Classification Search ................. 417/148; 422/68.1, 100, 103; 435/6, 287.6, 288.5
See application file for complete search history.

(56) References Cited

U.S. PATENT DOCUMENTS 2,404,869 A * 7/1946 Sorrentino .................. 417/148
4,339,232 A * 7/1982 Campbell ................... 417/148
4,444,548 A * 4/1984 Andersen et al. ............ 417/148
4,524,801 A * 6/1985 Magnasco et al. ........... 417/148
4,993,143 A 2/1991 Sidner et al.
5,429,734 A 7/1995 Gajar et al.
5,637,469 A 6/1997 Wilding et al.
5,639,423 A 6/1997 Northrup et al.
5,690,841 A 11/1997 Elderstig
5,922,591 A 7/1999 Anderson et al.
5,939,312 A 8/1999 Baier et al.
5,942,443 A 8/1999 Parce et al.
6,010,607 A 1/2000 Ramsey
6,046,056 A 4/2000 Parce et al.
6,116,863 A 9/2000 Ahn
6,168,948 B1 1/2001 Anderson et al.
6,261,431 B1 7/2001 Mathies et al.
6,267,858 B1 7/2001 Parce et al.
6,283,718 B1 9/2001 Prosperetti
6,376,291 B1 4/2002 Barlocchi et al.
6,394,759 B1 5/2002 Parce
6,403,367 B1 6/2002 Cheng et al.

(Continued)

FOREIGN PATENT DOCUMENTS

EP 1043770 A1 10/2000

(Continued)

OTHER PUBLICATIONS

Search Report, EP 03 10 3422, Dec. 4, 2003.

(Continued)

*Primary Examiner*—Charles G Freay
(74) *Attorney, Agent, or Firm*—Baker & McKenzie LLP

(57) ABSTRACT

A micropump includes a body (10) of semiconductor material, accommodating fluid-tight chambers (32), having an internal preset pressure, lower than atmospheric pressure. The fluid-tight chambers (32), sealed by a diaphragm (35) that can be electrically opened, are selectively openable using a first electrode (37) and second electrodes (38), accommodating between them portions of the diaphragm (35).

10 Claims, 9 Drawing Sheets

U.S. PATENT DOCUMENTS

| | | | | |
|---|---|---|---|---|
| 6,440,725 | B1 | 8/2002 | Pourahmadi et al. | |
| 6,453,928 | B1 | 9/2002 | Kaplan et al. | |
| 6,518,022 | B1 | 2/2003 | Sosnowski et al. | |
| 6,521,188 | B1 | 2/2003 | Webster | |
| 6,752,601 | B2 * | 6/2004 | Takeuchi et al. | 417/322 |
| 2001/0036672 | A1 | 11/2001 | Anderson et al. | |
| 2002/0017660 | A1 | 2/2002 | Villa et al. | |
| 2002/0022261 | A1 | 2/2002 | Anderson et al. | |
| 2002/0045244 | A1 | 4/2002 | Barlocchi et al. | |
| 2002/0055167 | A1 | 5/2002 | Pourahmadi et al. | |
| 2002/0060156 | A1 | 5/2002 | Mathies et al. | |
| 2002/0068334 | A1 | 6/2002 | Carrino et al. | |
| 2002/0068357 | A1 | 6/2002 | Mathies et al. | |
| 2002/0097900 | A1 | 7/2002 | Arena et al. | |
| 2002/0146330 | A1 | 10/2002 | Takeuchi | |
| 2003/0057199 | A1 | 3/2003 | Villa et al. | |

FOREIGN PATENT DOCUMENTS

| | | | |
|---|---|---|---|
| EP | 1049157 | A1 | 11/2000 |
| EP | 1130631 | A1 | 5/2001 |
| EP | 1123739 | A1 | 8/2001 |
| WO | WO-97/25531 | A | 7/1997 |

OTHER PUBLICATIONS

Voigt, P., et al., “Electrofluidic full-system modelling of a flap valve micropump based on Kirchhoffian network theory,” Sensors and Actuators, vol. 66(1-3):9-14, Apr. 1, 1998.

Zhang et al., “Automated and Integrated System for High-Throughput DNA Genotyping Directly from Blood”, Analytical Chemistry, vol. 71, No. 6, Mar. 1999.

* cited by examiner

MICROPUMP FOR INTEGRATED DEVICE FOR BIOLOGICAL ANALYSES

PRIOR RELATED APPLICATIONS

This application claims priority to Italian Patent Application No. TO2002A000809 filed on Sep. 17, 2002 in the name of STMicroelectronics S.r.l.

FEDERALLY SPONSORED RESEARCH STATEMENT

Not applicable.

REFERENCE TO MICROFICHE APPENDIX

Not applicable.

FIELD OF THE INVENTION

The invention relates to a micropump that can be advantageously used for an integrated device for analysis of nucleic acid or other biological specimen.

BACKGROUND OF THE INVENTION

Typical procedures for analyzing biological materials, such as nucleic acid, protein, lipid, carbohydrate, and other biological molecules, involve a variety of operations starting from raw material. These operations may including various degrees of cell separation or purification, cell lysis, amplification or purification, and analysis of the resulting amplification or purification product.

As an example, in DNA-based blood analyses samples are often purified by filtration, centrifugation or by electrophoresis so as to eliminate all the non-nucleated cells, which are generally not useful for DNA analysis. Then, the remaining white blood cells are broken up or lysed using chemical, thermal or biochemical means in order to liberate the DNA to be analyzed. Next, the DNA is denatured by thermal, biochemical or chemical processes and amplified by an amplification reaction, such as PCR (polymerase chain reaction), LCR (ligase chain reaction), SDA (strand displacement amplification), TMA (transcription-mediated amplification), RCA (rolling circle amplification), and the like. The amplification step allows the operator to avoid purification of the DNA being studied because the amplified product greatly exceeds the starting DNA in the sample.

If RNA is to be analyzed the procedures are similar, but more emphasis is placed on purification or other means to protect the labile RNA molecule. RNA is usually copied into DNA (cDNA) and then the analysis proceeds as described for DNA.

Finally, the amplification product undergoes some type of analysis, usually based on sequence or size or some combination thereof In an analysis by hybridization, for example, the amplified DNA is passed over a plurality of detectors made up of individual oligonucleotide detector fragments that are anchored, for example, on electrodes. If the amplified DNA strands are complementary to the oligonucleotide detectors or probes, stable bonds will be formed between them (hybridization). The hybridized detectors can be read by observation using a wide variety of means, including optical, electromagnetic, electromechanical or thermal means.

Other biological molecules are analyzed in a similar way, but typically molecule purification is substituted for amplification, and detection methods vary according to the molecule being detected. For example, a common diagnostic involves the detection of a specific protein by binding to its antibody. Such analysis requires various degrees of cell separation, lysis, purification and product analysis by antibody binding, which itself can be detected in a number of ways. Lipids, carbohydrates, drugs and small molecules from biological fluids are processed in similar ways. However, we have simplified the discussion herein by focusing on nucleic acid analysis, in particular DNA analysis, as an example of a biological molecule that can be analyzed using the devices of the invention.

The steps of nucleic acid analysis described above are currently performed using different devices, each of which presides over one part of the process. In other words, known equipment for nucleic acid analysis comprises a number of devices that are separate from one another so that the specimen must be transferred from one device to another once a given process step is concluded.

To avoid the use of separate devices, an integrated device must be used, but even in an integrated device the biological material specimen must be transferred between various treatment stations, each of which carries out a specific step of the process described above. In particular, once a fluid connection has been provided, preset volumes of the specimen and/or reagent species have to be advanced from one treatment station to the next.

To this aim, various types of micropumps are used. However, existing micropumps present a number of drawbacks. For example, in the most commonly used micropumps a membrane is electrically driven so as to suction a liquid in a chamber and then expel it. Inlet and outlet valves ensure a one-way flow. Membrane micropumps suffer, however, from the fact that they present poor tightness and allow leakage. In addition, the microfluid valves also leak and are easily obstructed. Consequently, it is necessary to process a conspicuous amount of specimen fluid because a non-negligible part thereof is lost to leakage. In practice, it is necessary to have available several milliliters of specimen fluid in order to obtain sufficient material for analysis. The use of large amounts of specimen fluid is disadvantageous both on account of the cost and because the processing times, in particular the duration of the thermal cycles, are much longer. In any case, imperfect tightness is clearly disadvantageous in the majority of applications and not only in DNA analysis equipment.

Other types of pumps, such as servo-assisted piston pumps or manually operated pumps, present better qualities of tightness, but currently are not integratable on a micrometric scale. Further common defects in known micropumps are represented by direct contact with the specimen undergoing analysis, which may give rise to unforeseeable chemical reactions, and high energy consumption.

The aim of the present invention is to provide a micropump free from the drawbacks described above.

SUMMARY OF THE INVENTION

The invention in one embodiment is a micropump having a body of semiconductor material with a plurality of fluid-tight chambers that are selectively openable, formed within said body and having a preset internal pressure. The micropump is fluidly connected to a microfluidic reactor, also in said body and being either integral with or welded to the micropump. The differential pressure in the micropump allows fluids to be driven from one location to another in the microreactor when the chambers are opened. Methods of manufacturing such a device are also included in the scope of the invention, as are methods of using such a device in biological analyses.

DESCRIPTION OF EMBODIMENTS OF THE INVENTION

The invention can be advantageously used in numerous applications, whenever it is necessary to move a fluid through microfluid connections. Hereinafter, reference will be made to DNA analysis devices, without this, however, limiting thereby the scope of the invention. In fact, the micropump can be employed with the analysis of any biological specimen.

EXAMPLE 1

Micropump

Figure 1:
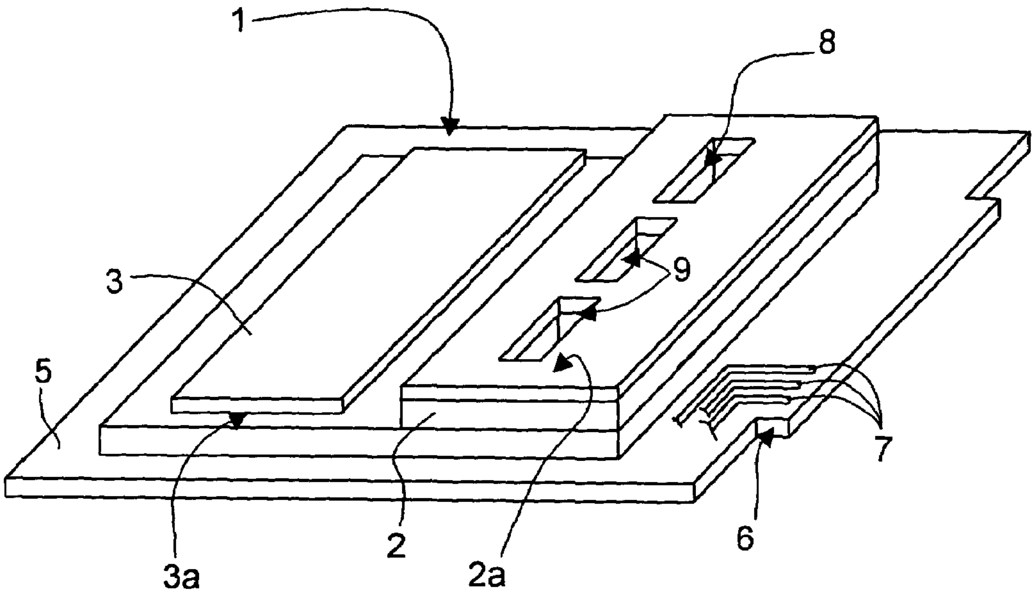
FIG. 1 is a three-quarter top perspective view of an integrated device incorporating a micropump according to a first embodiment of the invention.

As illustrated in FIG. 1, an integrated device for DNA analysis (Lab-On-Chip), designated, as a whole, by the reference number 1, comprises a microreactor 2 and a micropump 3. The microreactor 2 is carried on a printed-circuit board (PCB) 5 equipped with an interface 6 for connection to a driving and reading device (of a known type and not illustrated herein). In particular, input/output pins 7 of the microreactor 2 and of the micropump 3 are provided on the interface 6.

Figure 2:
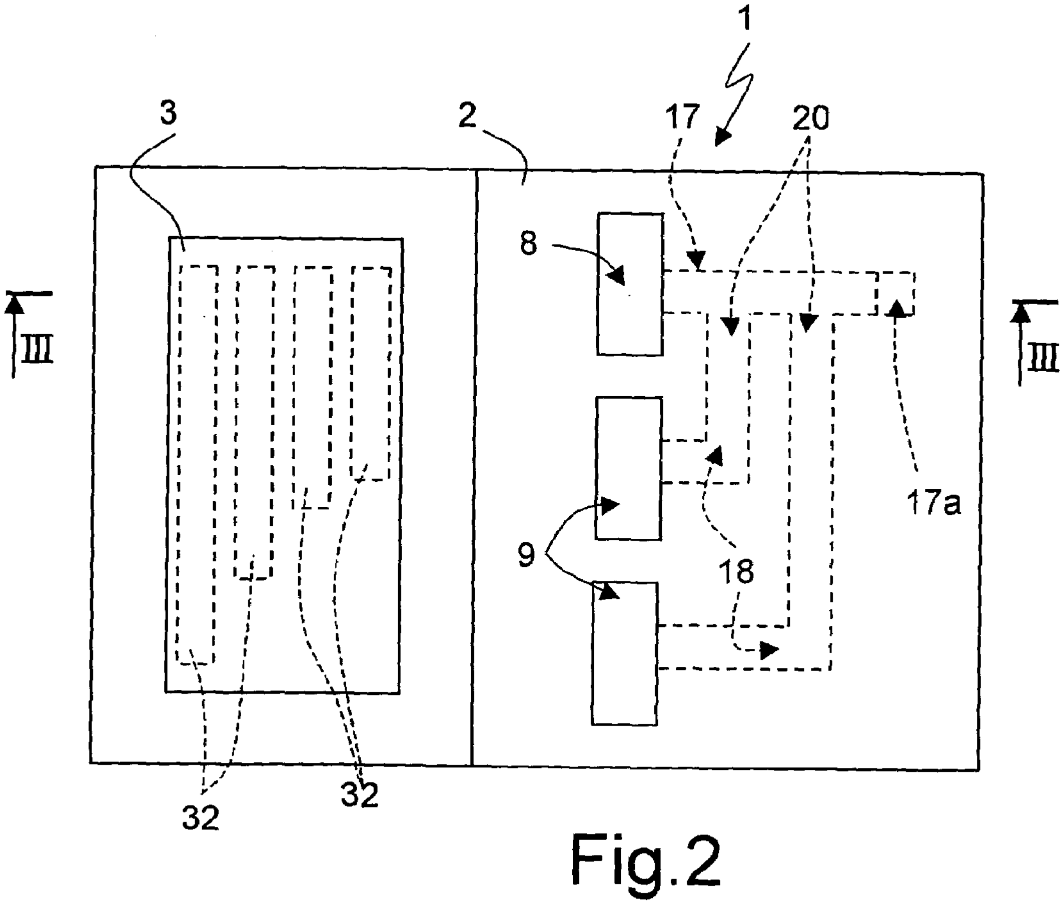
FIG. 2 is a top plan view of the device of FIG. 1.

The microreactor 2 has a specimen tank 8 and a plurality of reagent tanks 9 (two, in the example illustrated), which are open on one face 2*a* opposite to the PCB base 5 and accessible from outside. The micropump 3 is hermetically seal-welded on the microreactor 2 (see also FIG. 2).

Figure 3:
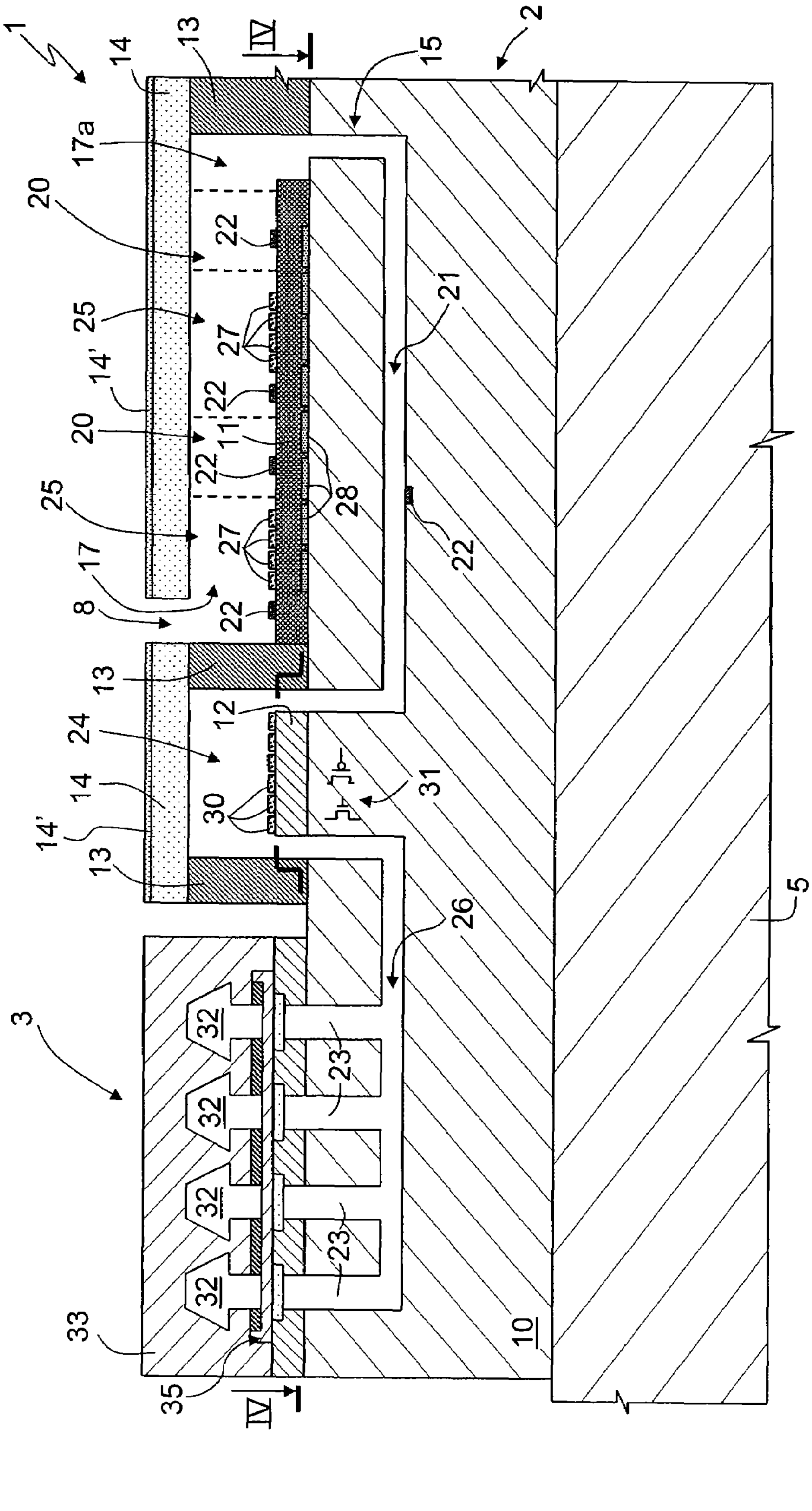
FIG. 3 is a cross-section through the device of FIG. 1, taken according to line III-III of FIG. 2.
Figure 4:
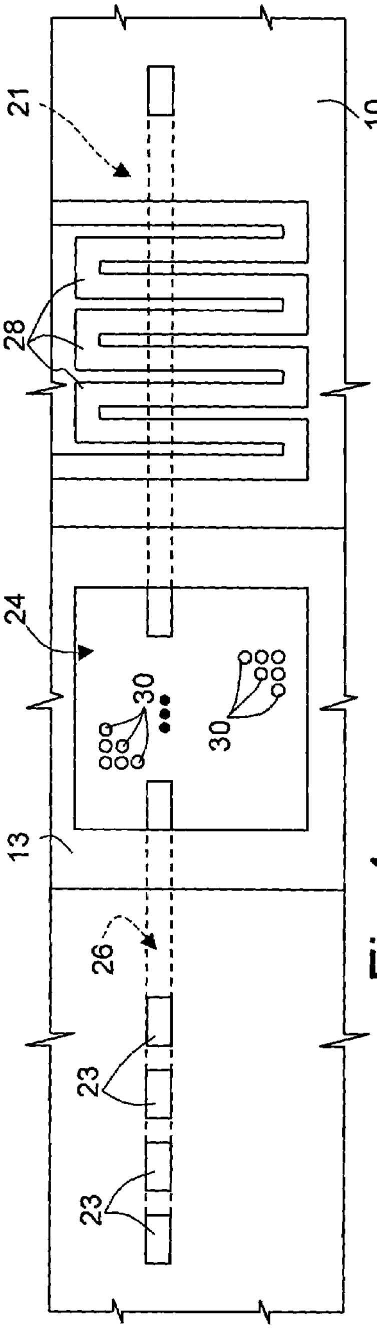
FIG. 4 is a top plan view of the device of FIG. 1, sectioned along line IV-IV of FIG. 3.

With reference to FIGS. 3 and 4, the microreactor 2 comprises a first body 10 of semiconductor material, for instance, monocrystalline silicon, and, on top thereof, a first and a second base 11, 12 of silicon dioxide, and a containment structure 13 of polymeric material, for example SU-8. In turn, the containment structure 13 is coated with a protective plate 14, which is open at the specimen tank 8 and the reagent tanks 9. The protective plate 14 is made using a transparent material coated with a conductive film 14', also transparent, for example, indium-tin oxide ITO. Alternatively, the protective plate 14 is of conductive glass. A hydraulic circuit 15 is defined inside the containment structure 13 and the first body 10. In greater detail, a pre-treatment channel 17, delimited laterally by the containment structure 13, at the top by the protective plate 14, and at the bottom by the first base 11, extends from the specimen tank 8, in the direction opposite to the micropump 3, substantially rectilinearly. Reagent channels 18 of preset length each connect a respective reagent tank 9 to the pre-treatment channel 17. Furthermore, at the outlet of the reagent channels 18, respective mixing chambers 20 are defined. One end 17*a* of the pre-treatment channel 17, opposite to the specimen tank 8, is connected to an amplification channel 21, which is buried in the first body 10. In particular, the amplification channel 21 extends into the first body 10 underneath the pre-treatment channel 17 and gives out into a detection chamber 24 formed in the containment structure 13 above the second base 12. A suction channel 26, which is also buried in the first body 10 and has an inlet into the detection chamber 24, extends underneath the micropump 3, and is connected via chimneys 23, as explained in greater detail hereinafter. In practice, the pre-treatment channel 17, the amplification channel 21, the detection chamber 24, and the suction channel 26 form a single duct through which a specimen of biological material to be analyzed is made to flow.

Stations for processing and analysis of the fluid are arranged along the pre-treatment channel 17 and the amplification channel 21; in proximity thereof sensors are provided for detecting the presence of fluid 22 and controlling advance of the specimen to be analyzed. In detail, two dielectrophoresis cells 25 are located in the pre-treatment channel 17 immediately downstream of the specimen tank 8 and, respectively, between the mixing chambers 20. The dielectrophoresis cells 25 comprise respective grids of electrodes 27 arranged above the first base 11 and forming electrostatic cages with respectively facing portions of the protective plate 14. The grid of electrodes 27 are electrically connected to a control device (of a known type and not illustrated) through connection lines (not illustrated either) and enable electric fields to be set up having an intensity and direction that are controllable inside the dielectrophoresis cells 25.

A heater 28 is arranged on the first body 10 above the amplification channel 21, is embedded in the first base 11 of silicon dioxide and enables heating of the amplification channel 21 for carrying out thermal PCR processes (see also FIG. 4).

Located downstream of the amplification channel 21 is the detection chamber 24, which, as mentioned previously, is formed in the containment structure 13 and is delimited at the bottom by the second base 12 and at the top by the protective plate 14. An array of detectors 30, here of the cantilever type, is arranged on the second base 12 and can be read electronically. In addition, a CMOS sensor 31, associated to the detectors 30 and illustrated only schematically in FIG. 3, is provided in the first body 10 underneath the detection chamber 24. In practice, then, a CMOS sensor 31 is connected directly to the detectors 30 without interposition of connection lines of significant length.

The suction channel 26 extends from the detection chamber 24 underneath the micropump 3, and is connected to the latter by the chimneys 23.

Figure 5:
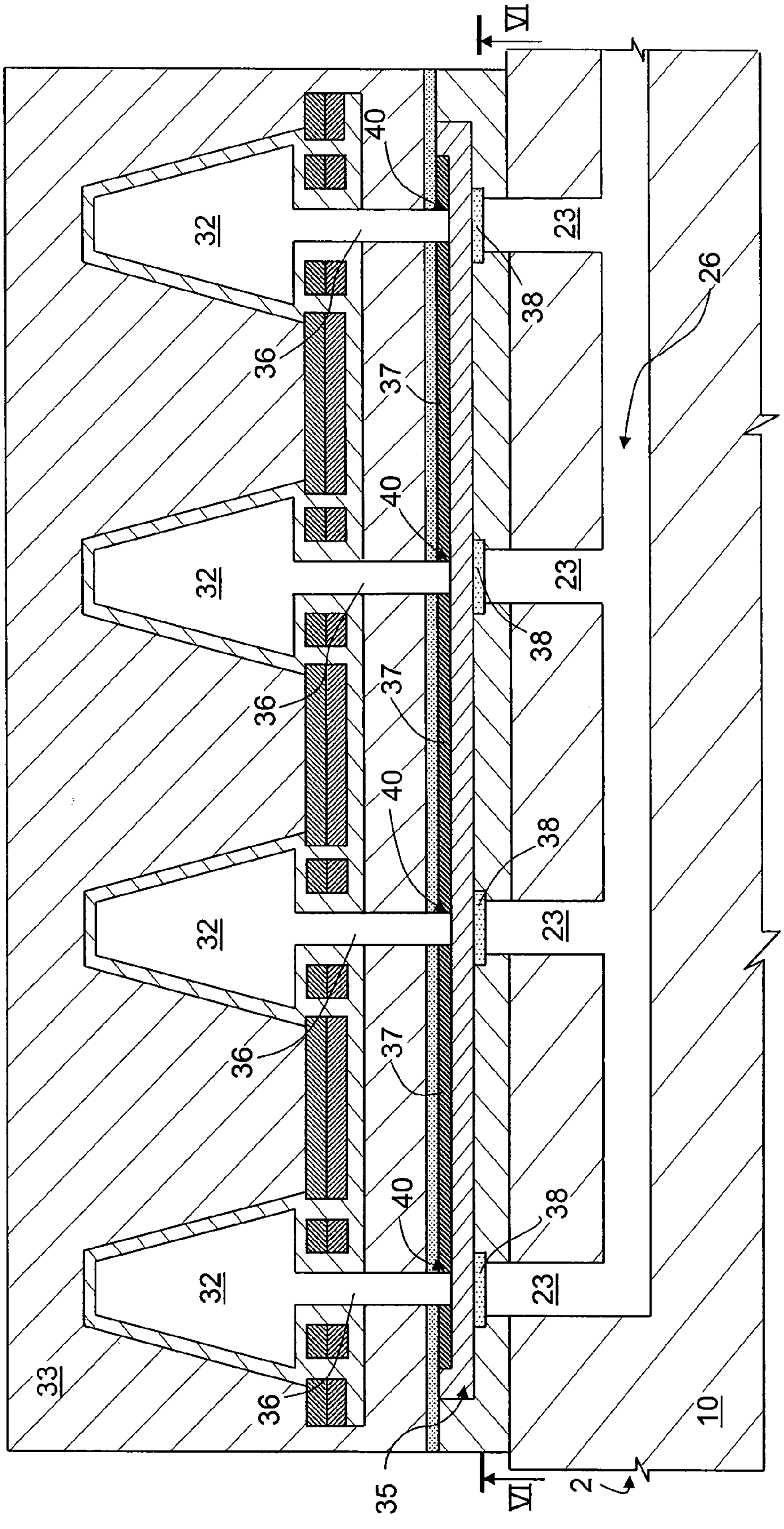
FIG. 5 is an enlarged scale view of the micropump of FIGS. 1 to 3.

The micropump 3, which for convenience is illustrated in FIG. 3 in a simplified way, is shown in detail in FIG. 5. The micropump 3 comprises a second body 33 of semiconductor material, for example silicon, accommodating a plurality of fluid-tight chambers 32. In greater detail, the fluid-tight chambers 32 have a prismatic shape, extend parallel to each other and to a face 34*a* of the second body 33, and have predetermined dimensions, as will be clarified hereinafter. In addition, the fluid-tight chambers 32 are sealed by a diaphragm 35 of silicon dioxide, which closes respective inlets 36 of the fluid-tight chambers 32 so as to maintain a preset pressure value, considerably lower than standard atmospheric pressure (for example, 100 mtorr). Preferably, the diaphragm 35 has a thickness of not more than 1 μm.

As illustrated in FIGS. 3 and 5, the inlets 36 of the fluid-tight chambers 32 are aligned to respective chimneys 23 so as to be set in fluid connection with the suction channel 26 once the diaphragm 35 has been broken. Furthermore, since the micropump 3 is hermetically bonded to the microreactor 2, the fluid-tight chambers 32 can be connected with the outside world only through the duct formed by the suction channel 26, the amplification channel 21, the pre-treatment channel 17, and the reagent channels 18.

Figure 6:
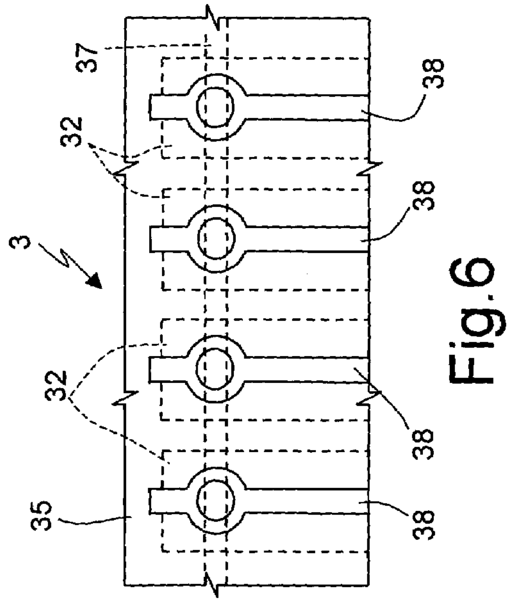
FIG. 6 is a bottom view of the micropump illustrated in FIG. 5, sectioned along line VI-VI of FIG. 5.

The micropump 3 is then provided with electrodes for opening the fluid-tight chambers 32. In particular, a first activation electrode 37 is embedded in the diaphragm 35 and extends in a transverse direction with respect to the fluid-tight chambers 32 near the inlets 36 (see also FIG. 6). In greater detail, the first activation electrode 37 is perforated at the inlets 36 so as not to obstruct the latter. Second activation electrodes 38 are arranged on a face of the diaphragm 35 opposite to the first activation electrode 37 and extend substantially parallel to the fluid-tight chambers 32. In addition, each second electrode 38 is superimposed to a first electrode 37 at the inlet 36 of a respective fluid-tight chamber 32, thus forming a plurality of capacitors 40 having respective portions of the diaphragm 35 as dielectric.

Figure 7:
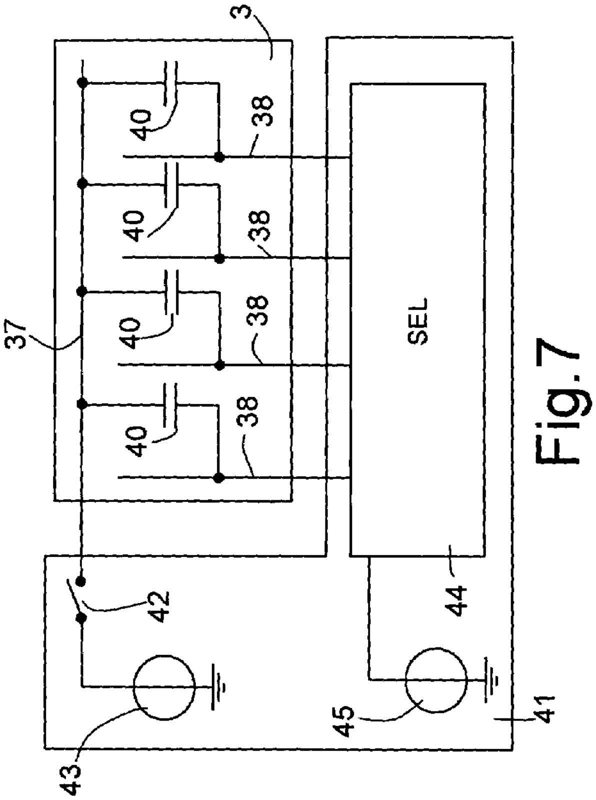
FIG. 7 is a simplified circuit diagram of the micropump of FIG. 1.

FIG. 7 illustrates a simplified electrical diagram of the micropump 3 and of a control circuit 41. In practice, the first activation electrode 37 may be connected, via a switch 42, to a first voltage source 43, supplying a first voltage V1. Through a selector 44, the second activation electrodes 38 can be selectively connected to a second voltage source 45, which supplies a second voltage V2, preferably, of opposite sign to the first voltage V1. In this way, it is possible to select each time one of the capacitors 40 and to apply to its terminals a voltage equal to V1-V2 higher than the breakdown voltage of the diaphragm 35, which functions as a dielectric. Consequently, the corresponding fluid-tight chamber 32 is selectively opened and set in fluid connection with the suction channel 26.

At the start of the DNA analysis process, a (fluid) specimen of raw biological material is introduced inside the specimen tank 8, while the reagent tanks 9 are filled with respective chemical species necessary for the preparation of the specimen, for instance, for subsequent steps of lysis of the nuclei. In this situation, the inflow of the air from the outside environment towards the inside of the pre-treatment channel 17, the reagent channels 18, and the amplification channel 21 is prevented.

Next, the micropump 3 is operated by breaking the portion of the diaphragm 35 that seals one of the fluid-tight chambers 32. In practice, by opening the vacuum cell 32, a negative pressure is created and then, after the air present has been suctioned out, the specimen and the reagents previously introduced into the tanks 8, 9 are suctioned along the duct formed by the pre-treatment channel 17, the reagent channels 18, the amplification channel 21, the detection chamber 24, and the suction channel 26. The moved fluid mass and the covered distance depend upon the pressure value present in the fluid-tight chamber 32 before opening and upon the dimensions of the fluid-tight chamber 32. In practice, the first vacuum cell 32 that is opened is sized so that the specimen will advance up to the dielectrophoresis cell 25 arranged at the inlet of the pre-treatment channel 17, and the reagents will advance by preset distances along the respective reagent channels.

After a first dielectrophoretic treatment has been carried out, the other fluid-tight chambers 32 of the pump 3 are opened in succession at preset instants so as to cause the specimen to advance first along the pre-treatment channel 17 and then along the amplification channel 21 up to the detection chamber 24. In practice, therefore, the micropump 3 is used as a suction pump that can be operated according to discrete steps. The specimen, whose advance is controlled also by the presence of sensors 22, is prepared in the pre-treatment channel 17 (separation of the reject material in the dielectrophoresis cells 25 and lysis of the nuclei in the mixing chambers 20), and in the amplification channel 21, where a PCR treatment is carried out. Then, in the detection chamber 24, hybridization of the detectors 30 takes place, and the latter are then read by the CMOS sensor 31.

Figure 8:
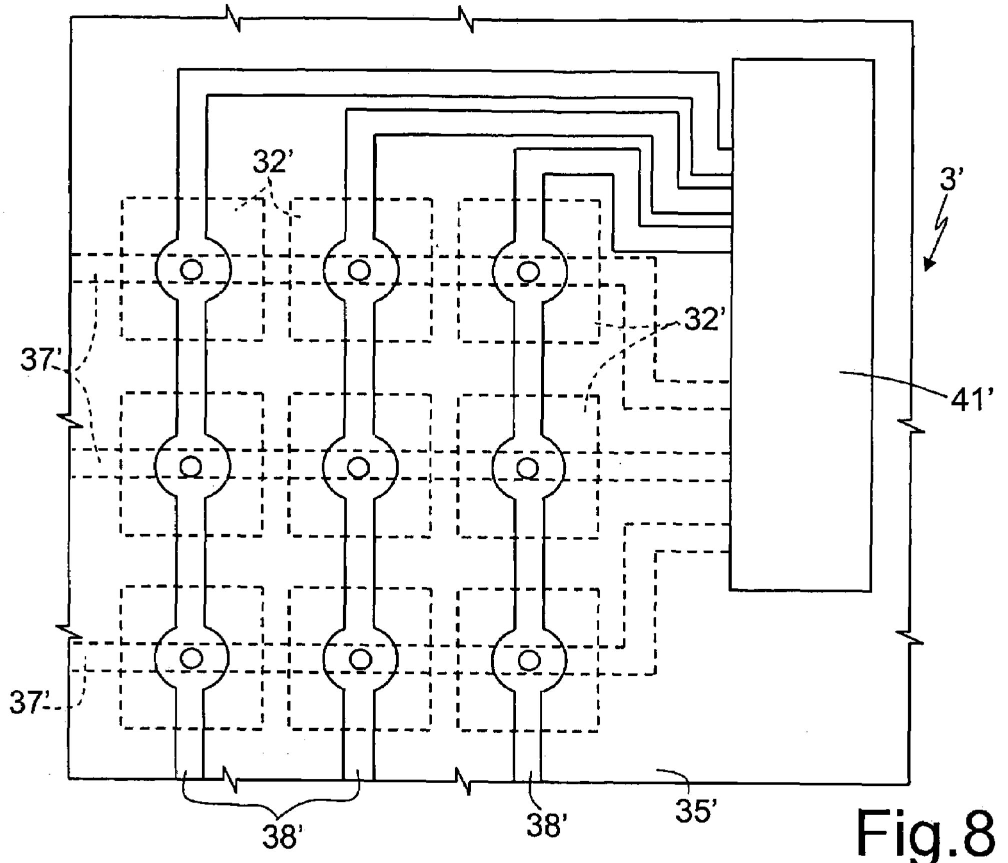
FIG. 8 is a partial bottom view of a micropump according to a second embodiment of the present invention, in which some parts have been removed, for clarity.
Figure 9:
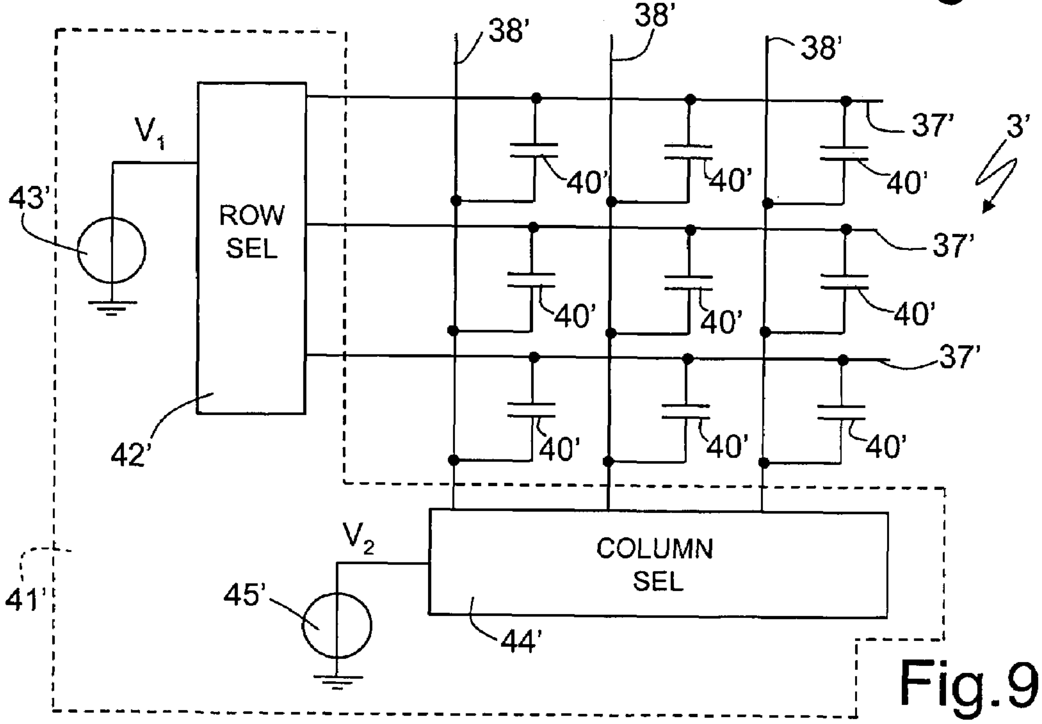
FIG. 9 is a simplified circuit diagram of the micropump of FIG. 8.

According to a different embodiment of the invention, illustrated in FIGS. 8 and 9, a micropump 3' comprises fluid-tight chambers 32' arranged in rows and columns so as to from a matrix array. In this case, the micropump 3' comprises as many first activation electrodes 37" as are the matrix rows, and as many second activation electrodes 38" as are the matrix columns. Capacitors 40', having as a dielectric respective portions of a diaphragm 40', which seal the fluid-tight chambers 32', are formed in the regions where the first activation electrodes 37' and the second activation electrodes 38' cross over one another. Furthermore, a control circuit 41', integrated on the micropump 3', comprises a row selector 42', for selectively connecting one of the first electrodes 37' to a first voltage source 43', and a column selector 44', for selectively connecting one of the second electrodes 38' to a second voltage source 45'.

Figure 10:
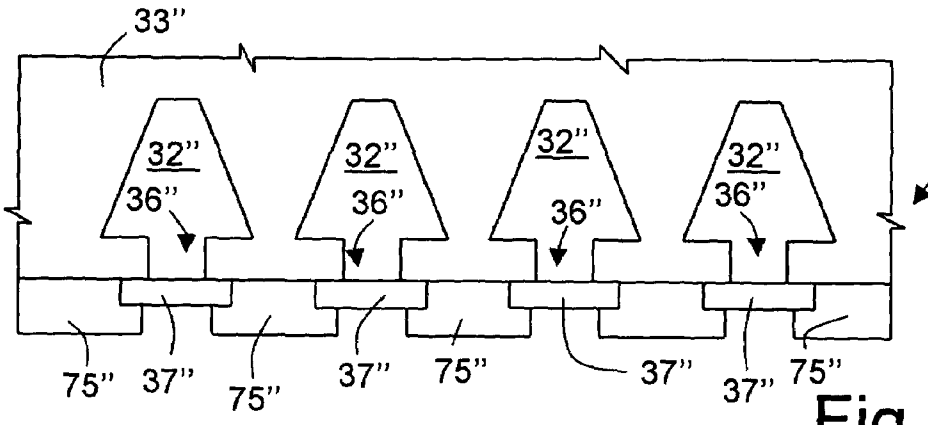
FIG. 10 is a cross-section of a micropump according to a third embodiment of the present invention.
Figure 11:
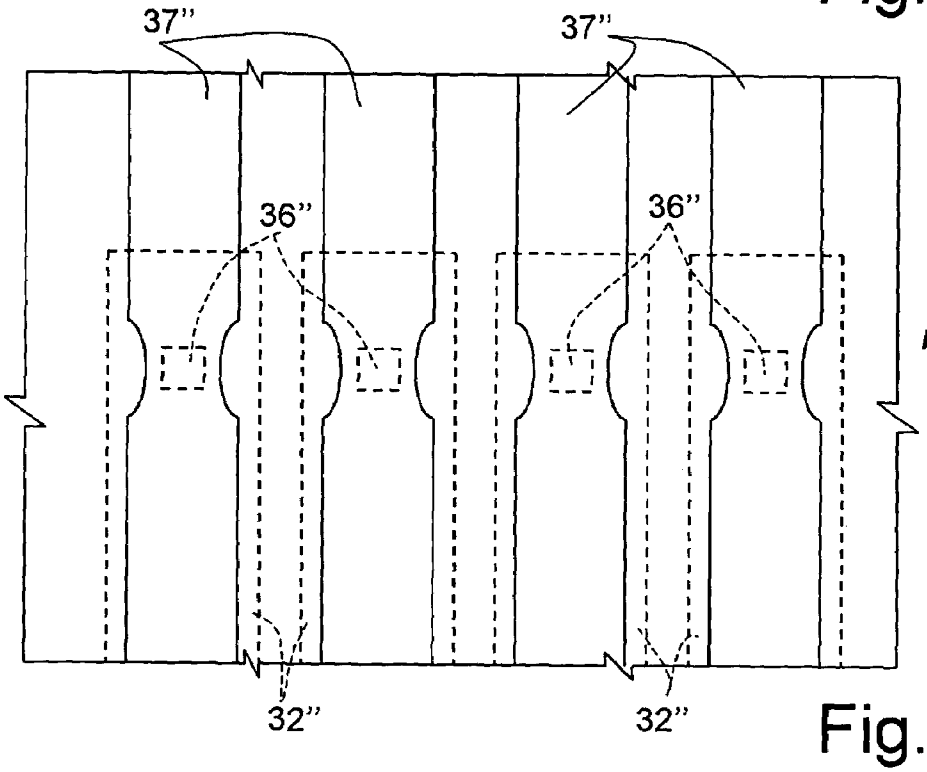
FIG. 11 is a bottom view of the micropump of FIG. 10.
Figure 12:
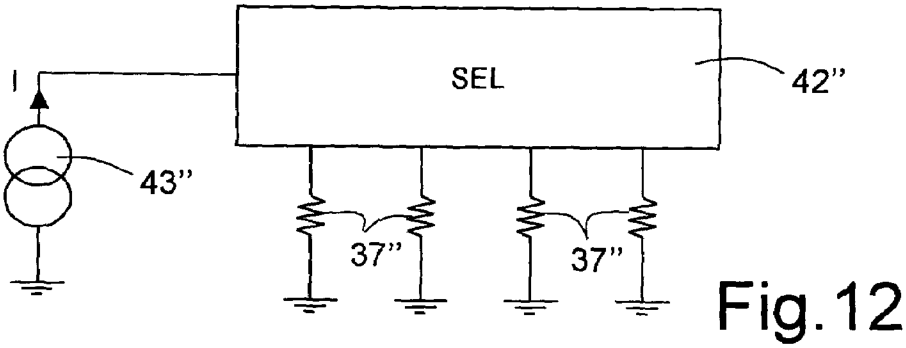
FIG. 12 is a simplified circuit diagram of the micropump of FIG. 11.
Figure 13:
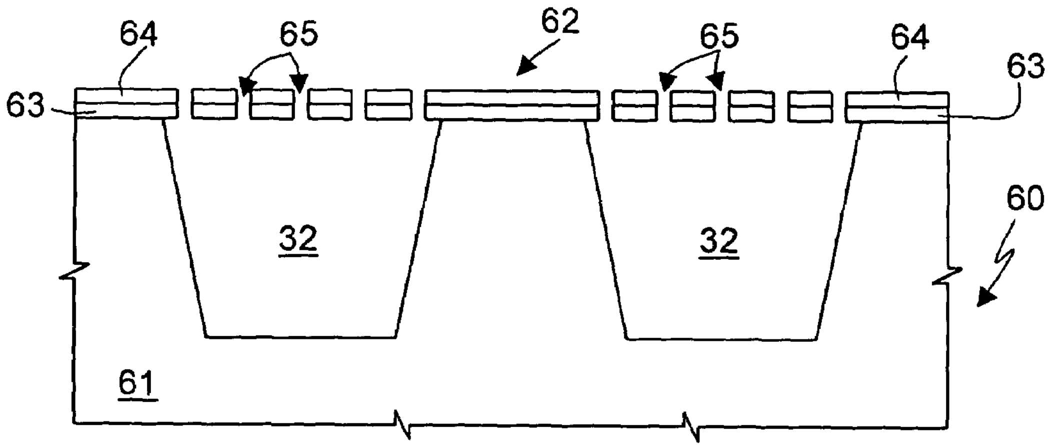
FIGS. 13 to 20 are cross-sections through a semiconductor wafer in successive steps of a process for manufacturing a second part of the device according to the present invention.
Figure 14:
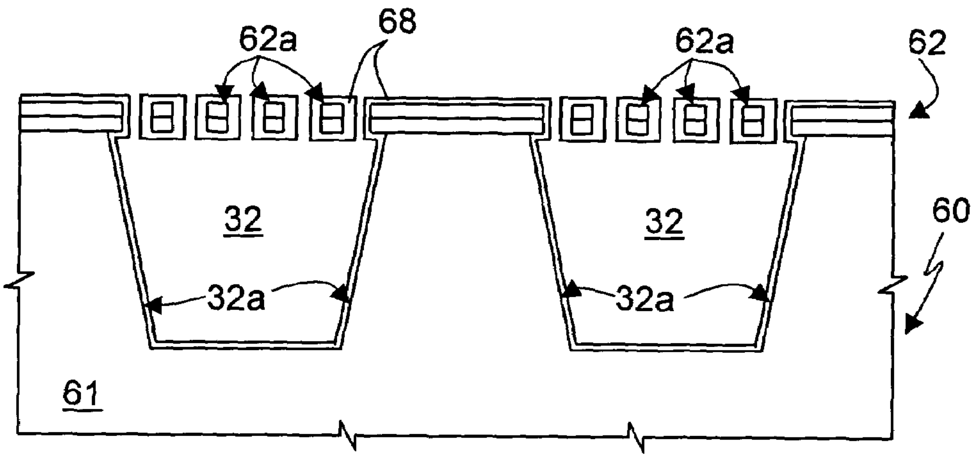
Figure 15:
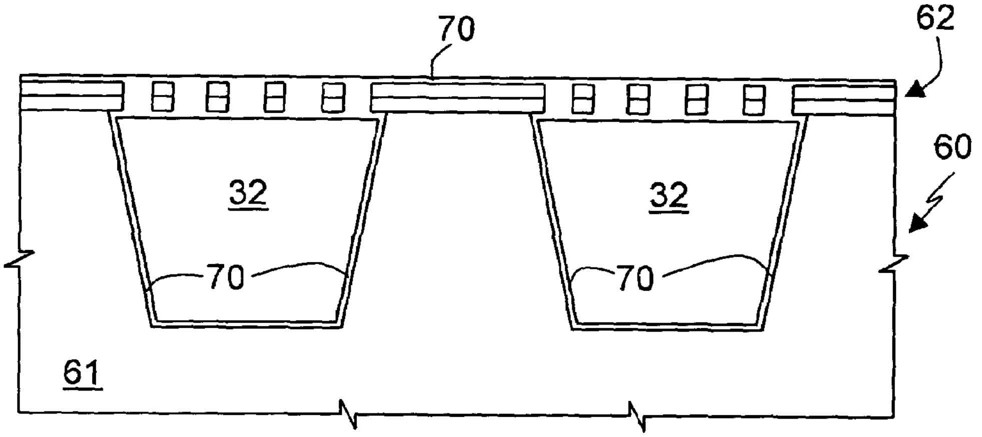
Figure 16:
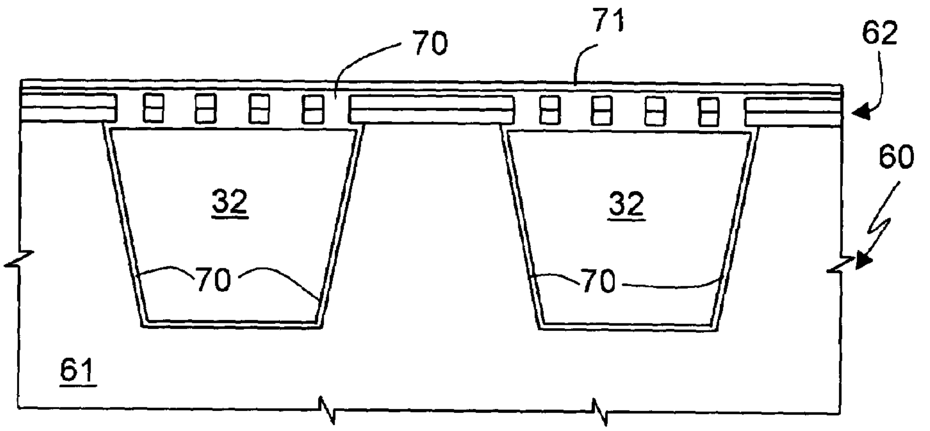

According to a further variant, illustrated in FIGS. 10 and 11, a micropump 3" comprises a body 33" accommodating fluid-tight chambers 32". In this case, each fluid-tight chamber 32" has an inlet 36", directly sealed by a respective aluminum electrode 37". In practice, the electrodes 32" form conductive diaphragms, which close respective fluid-tight chambers 32". In addition, near the fluid-tight chambers 32", the electrodes 37" narrow and have preferential melting points. Consequently, when a current source 43", which can be selectively connected to one of the electrodes 37" through a selector 42" (see FIG. 12), injects a preset current I higher than a melting threshold, the preferential melting points of the electrodes 37" yield first, opening the corresponding fluid-tight chambers 32" (in FIG. 12, the electrodes 37" are represented by symbols for resistors).

The integrated device according to the invention has numerous advantages. First, the micropump can be easily connected in a fluid-tight way to a hydraulic circuit, as for the duct formed in the microreactor described above. In addition, there is no need of valves because the micropump by itself is able to move the fluid in the hydraulic circuit, causing it to advance in a single direction. In this way, all the leakage of specimen fluid, which afflicts traditional micropumps and which are normally due to imperfect fluid tightness and/or to evaporation, are eliminated. In particular, in case of DNA analysis, minimal amounts of raw biological material are sufficient, i.e., of the order of microlitres or even nanolitres: Clearly, the use of smaller amounts of specimen fluid has the advantage of reducing both costs and treatment time (shorter thermal cycles). Further advantages are the absence of any direct contact between the micropump and the fluid, which rules out any risk of unforeseeable chemical reactions, the absence of moving parts, and the low energy consumption.

EXAMPLE 2

Manufacture of Micropump

In addition to the above advantages, the micropump can be built in a simple way and at a low cost, following, for example, the process illustrated hereinafter with reference to FIGS. 13 to 20.

On a semiconductor wafer 60 having a substrate 61, a hard mask 62 is initially formed, and comprises a silicon dioxide layer 63 and a silicon nitride layer 64. The hard mask 62 has groups of slits 65, substantially rectilinear and parallel to each other. The substrate 61 is then etched using tetramethyl ammonium hydroxide (TMA) and the fluid-tight chambers 32 are dug through respective groups of slits 65.

Next (see FIG. 14), a polysilicon layer 68 is deposited, which coats the surface of the hard mask 62 and the walls 32*a* of the fluid-tight chambers 32. In addition, the polysilicon layer 68 incorporates portions 62*a* of the hard mask 62, suspended after forming the fluid-tight chambers 32. The polysilicon layer 68 is then thermally oxidized (see FIG. 15) so as to form a silicon dioxide layer 70, which grows also outwards and closes the slits 65.

Figure 17:
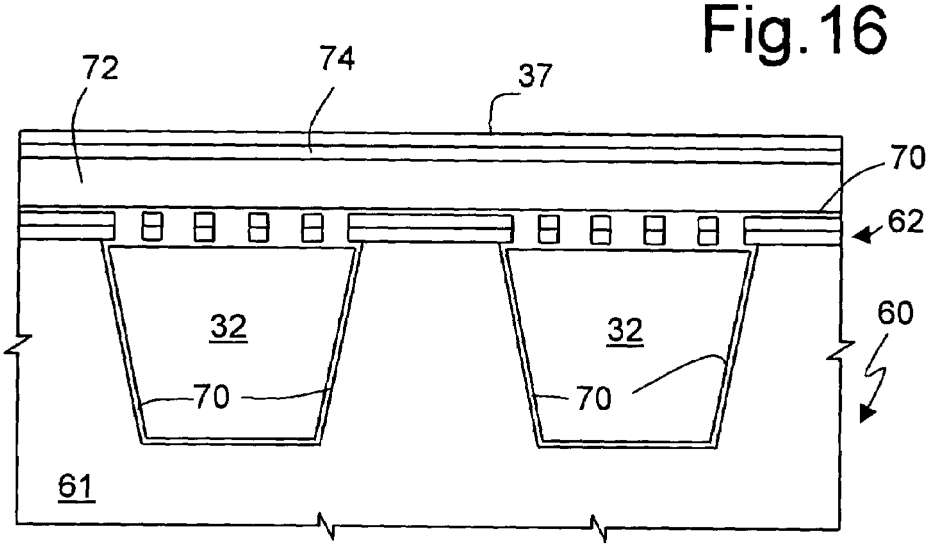
Figure 18:
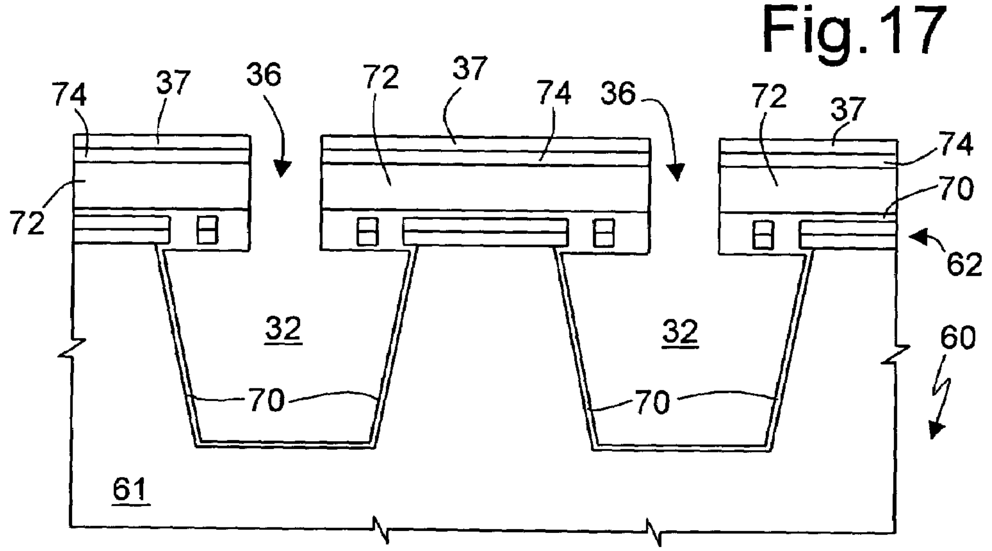

After depositing a germ layer 71 of polysilicon (see FIG. 16), an epitaxial layer 72 is grown and thermally oxidized on the surface so as to form an insulating layer 74 (see FIG. 17). On top of the insulating layer 74, a strip of aluminum is then deposited and forms the first activation electrode 37. Then, an STS etch is performed. As illustrated in FIG. 18, in this step the first activation electrode 37, the insulating layer 74, the epitaxial layer 72 and the hard mask 62 are perforated, and the inlets 36 of the fluid-tight chambers 32 are defined and thus re-opened.

Figure 19:
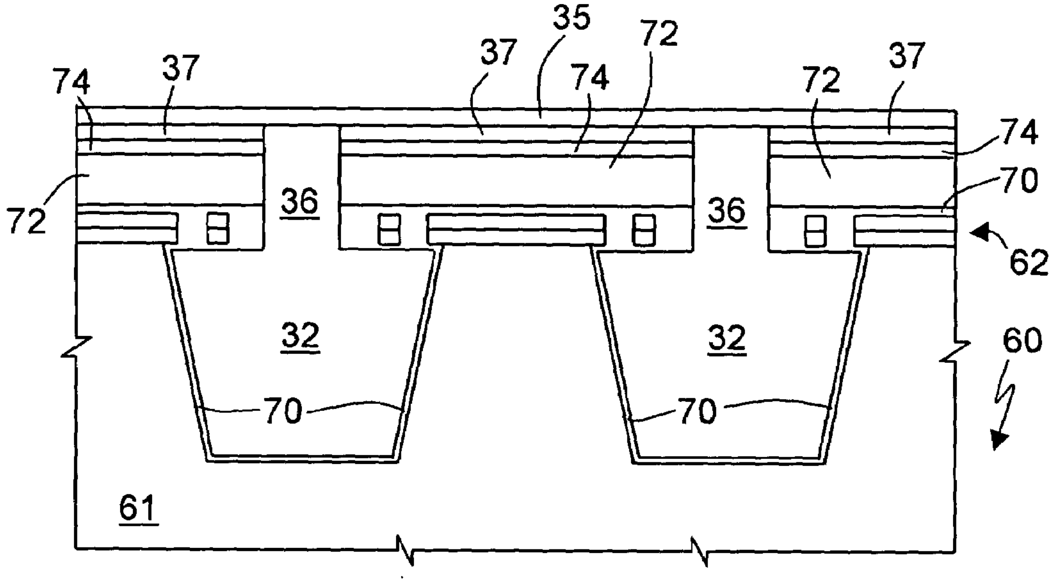

By depositing silicon dioxide at controlled pressure lower than atmospheric pressure (for example, 100 mtorr), the diaphragm 35 is then formed, thus incorporating the first activation electrode 37 and sealing the fluid-tight chambers 32 (see FIG. 19). Consequently, inside the fluid-tight chambers 32, the pressure imposed during deposition of the diaphragm 35 is maintained.

Figure 20:
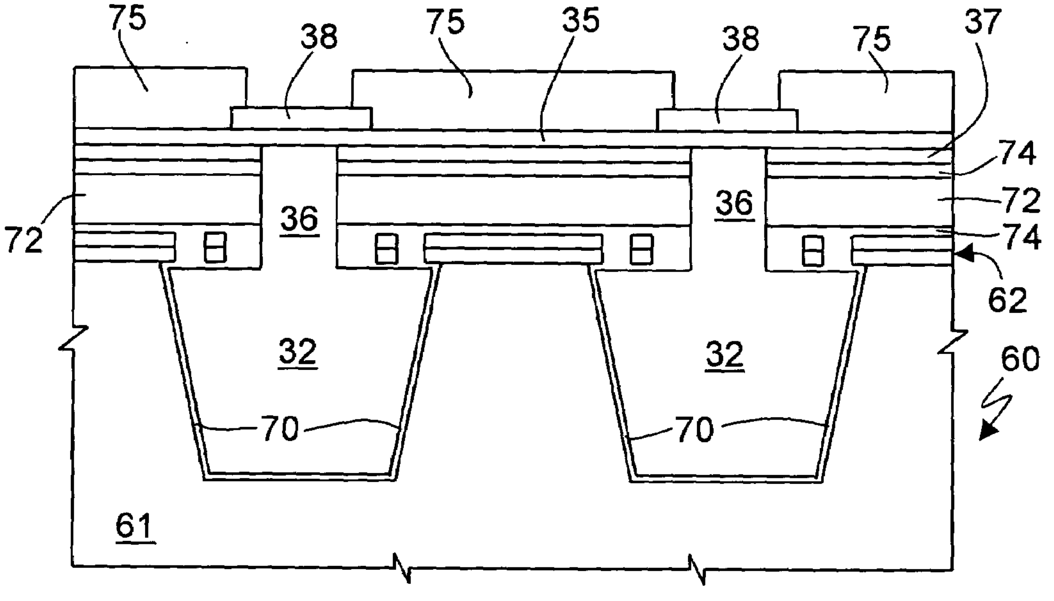

Next, by further depositing aluminum, the second activation electrodes 38 are formed, and a protective resist layer 75 is then formed, which is open above the second activation electrodes 38 (see FIG. 20).

Finally, the semiconductor wafer 60 is cut so as to obtain a plurality of dice, each containing a micropump 3, bonded to a respective microreactor 2. Thereby, the structure illustrated in FIGS. 3 and 5 is obtained.

Alternatively, after forming the epitaxial layer and the insulation layer, the electrodes 37" are deposited, having defined preferential melting points. Then a protective resist layer 75" is deposited, leaving exposed the preferential breakdown points, and the micropump 3" illustrated schematically in FIG. 10 is obtained.

Finally, it is clear that modifications may be made to the micropump described herein, without departing from the scope of the present invention.

First, the micropump could be of the force-pump type instead of a suction-pump type. In this case, the pressure inside the fluid-tight chambers is higher than the operating pressure of the environment in which the micropump is to be used.

In addition, the micropump may comprise a different number of fluid-tight chambers according to the number of steps required by the treatment. The fluid-tight chambers may differ also as regards their shape, dimensions, and arrangement.

What is claimed is:

1. A micropump, comprising a body of semiconductor material, characterized by a plurality of fluid-tight chambers, selectively openable, formed within said body and having a preset internal pressure substantially different from standard atmospheric pressure, and at least one capacitor comprising a dielectric diaphragm arranged between a first electrode and a second electrode, wherein at least one of the fluid-tight chambers is sealed by the dielectric diaphragm.

2. The micropump according to claim 1, characterized in that each of said fluid-tight chambers is sealed by at least one diaphragm, openable electrically.

3. The micropump according to claim 1, characterized in that said diaphragm is of silicon dioxide.

4. The micropump according to claim 3, characterized in that said diaphragm has a thickness not greater than 1 μm.

5. The micropump according to claim 1, characterized by a first voltage source, connectable to said first electrode of said micropump and supplying a first voltage (V1), and a second voltage source, selectively connectable to one of said second electrodes of said micropump and supplying a second voltage (V2).

6. A method of amplification, comprising amplifying a target nucleic acid in an integrated microfluidic reactor, wherein a fluid comprising the target nucleic acid is moved through the microfluidic reactor using the micropump of claim 5.

7. A method of biological analysis, comprising analyzing a target biological molecule in an integrated microfluidic reactor, wherein a fluid comprising the target biological molecule is moved through the microfluidic reactor using the micropump of claim 5.

8. The micropump according to claim 1, characterized in that said chambers have a preset internal pressure substantially lower than standard atmospheric pressure.

9. The micropump according to claim 8, characterized in that said chambers have a preset internal pressure of about 100 mtorr.

10. A microfluidic device comprising:

a) a microfluidic circuit; and b) a micropump, for moving a fluid through the microfluidic circuit, wherein the micropump comprises a body of semiconductor material, and a plurality of selectively openable fluid-tight chambers formed within said body and wherein a pressure differential is present between the fluid-tight chambers and the microfluidic circuits, wherein at least one of the fluid-tight chambers is sealed by a capacitor comprising a dielectric diaphragm arranged between a first electrode connected to a first voltage source and a second electrode connected a second voltage source.

* * * * *